United States Patent [19]

Alhede et al.

[11] Patent Number: 5,223,619
[45] Date of Patent: Jun. 29, 1993

[54] PROCESS FOR THE PREPARATION OF 9-SUBSTITUTED GUANINE DERIVATIVES

[75] Inventors: Borge Alhede, Greve Strand; Finn P. Clausen, Allerod; Jorgen Juhl-Christensen, Greve Strand; Klaus K. McCluskey, Slangerup; Herbert Preikschat, Birkerod, all of Denmark

[73] Assignee: A/S Gea Farmaceutisk Fabrik, Frederiksberg, Denmark

[21] Appl. No.: 761,890

[22] PCT Filed: Mar. 19, 1990

[86] PCT No.: PCT/DK90/00077

§ 371 Date: Sep. 20, 1991

§ 102(e) Date: Sep. 20, 1991

[87] PCT Pub. No.: WO90/11283

PCT Pub. Date: Oct. 4, 1990

[30] Foreign Application Priority Data

Mar. 20, 1989 [DK] Denmark ............... 1354/89

[51] Int. Cl.$^5$ .................. C07D 473/02; A61K 31/52
[52] U.S. Cl. .................. 544/276; 544/277; 548/326.5; 548/311.1
[58] Field of Search ................. 544/276, 277

[56] References Cited

U.S. PATENT DOCUMENTS 4,602,089 7/1986 Simm et al. .................. 544/276

FOREIGN PATENT DOCUMENTS 0126813 12/1984 European Pat. Off. .
0219838 4/1987 European Pat. Off. .
0180473 10/1983 Japan .

OTHER PUBLICATIONS

Houben-Weyl 5 1b, 1972, Dr. Otto Klein: "Olefine durch Dimerisierung bifunktioneller Verbindungen", pp. 418-420.

Nucleic Acids Research, vol. 3, No. 1, 1986, A. Yamazaki et al.: "Synthesis of guanosine and its derivatives from 5-amino-1-$\beta$-D-ribofuranolsyl-4-imidazolecarboxamide. IV. A new route to guanosine via cyanamide derivative".

J. Chem. Soc. Perkin Trans. 1, 1987, C. B. Reese et al.: "The conversion of the 2',3'-O-isopropylidene derivative of 5-amino-1-$\beta$-D-ribofuranosylmidazole-r-carboxamide (AICA RIBOSIDE) into 2',3'. -O-isopropylidene-isoquanosine", see pp. 1527-1531.

J. Org. Chem. vol. 51, 1986, Michael P. Groziak et al.: "A New and Efficient Synthesis of Guanosine".

*Primary Examiner*—Nicholas S. Rizzo
*Attorney, Agent, or Firm*—Oblon, Spivak, McClelland, Maier & Neustadt

[57] ABSTRACT

A process for the preparation of 9-substituted quanine derivatives of general formula (I), in which R is $C_1$-$C_4$-alkyl optionally substituted with one or more hydroxy groups, or R is ($\alpha$), benzyl, ribosyl, 2'-deoxyribosyl or $(CH_2)_n$-$OR^1$ where n is 1 or 2, and $R^1$ is $CH_2CH_2OH$ or ($\beta$) or salts thereof, in which a 1-substituted5-(thiocarbamoyl)amino-1H-imidazole-4-carboxamide of general formula (III), where R has the same meaning as in formula (I), is cyclized: a) by treatment with a heavy metal salt of the group of Cu-, Ag-, Pb- and Hg-salts in an aqueous alkaline medium containing at least for equivalents of OH-ions at a temperature form about 0° C. to the reflux temperature, or b) by treatment with a peroxy compound in an aqueous alkaline medium at a temperature of about 0°-30° C., whereafter (I) is isolated by treatment with a acid and, if desired, is converted into a salt. The invention further comprises intermediates for use in the preparation of the above-mentioned compounds.

3 Claims, No Drawings

PROCESS FOR THE PREPARATION OF 9-SUBSTITUTED GUANINE DERIVATIVES

TECHNICAL FIELD

The present invention relates to a process for the preparation of 9-substituted guanine derivatives of the general formula I

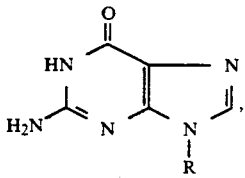

in which R is $C_1$–$C_4$-alkyl optionally substituted with one or more hydroxy groups, or R is

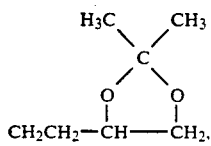

benzyl, ribosyl, 2'-deoxyribosyl or $(CH_2)_n$-$OR^1$ where n is 1 or 2, and $R^1$ is $CH_2CH_2OH$ or

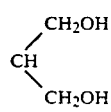

or salts thereof.

Compounds of this type are therapeutically active compounds having an antiviral activity or are intermediates for the preparation of compounds of interest in gene technology.

BACKGROUND ART

It is known (J. Org. Chem. 51 1277–1282 (1986)) that guanosine can be prepared from 4-carboxamide-5-amino-1-ribofuranosyl imidazole by a process in three steps which involves condensation with carbodiimide derivatives, cyclization with PdO present and treatment with $NH_4OH$. This process is not attractive because it requires use of the toxic compound phosgene to prepare the carbodiimide derivatives, and because the cyclization and the subsequent treatment with $NH_4OH$ take a very long time.

It is also known that the compound of formula I in which R is H can be prepared by a process in which the compound of formula II

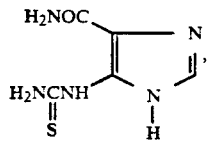

is first methylated to form the corresponding thiometyl compound which is then cyclized in alkaline medium (A. Yamazaki, Nucl. Acids. Res., 3, 1976, 251–259). This process has the drawback that the toxic and evil swelling methylmercaptane is formed as a by-product, and besides the yield is poor. It is reported in the article that cyclization of the compound II using the heavy metal salt HgO is not possible.

DISCLOSURE OF THE INVENTION

However, surprisingly we have found that it is possible to carry out cyclization of $N^1$-substituted derivatives of compounds of formula II without methylating first and using a heavy metal salt in aqueous alkaline medium or using peroxy compounds.

The process according to the invention is characterised in that a 1-substituted 5-(thiocarbamoyl)amino-1H-imidazole-4-carboxamide of the general formula III

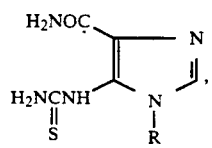

where R has the same meaning as in formula I is cyclized a) by treatment with a heavy metal salt of the group of Cu-, Ag-, Pb- and Hg-salts in an aqueous alkaline medium containing at least four equivalents of $OH^-$ ions at a temperature from about 0° C. to the reflux temperature, or b) by treatment with a peroxy compound in an aqueous alkaline medium at a temperature of about 0°–30° C. in the presence of tungstate ions as a catalyst.

whereafter I is isolated by treatment with acid and, if desired, is converted into a salt.

The starting compounds of formula III

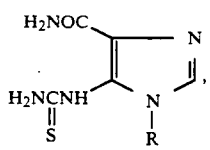

in which R is $C_1$–$C_4$-alkyl optionally substituted with one or more hydroxy groups, or R is

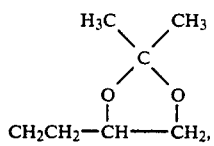

benzyl, ribosyl, 2'-deoxyribosyl or $(CH_2)_n$-$OR^1$, where n is 1 or 2, and $R^1$ is $CH_2CH_2$ or

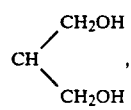

or salts thereof are novel compounds, and the invention therefore further comprises these compounds as intermediates for the preparation of 9-substituted guanine derivatives of formula I.

The starting materials of formula III can be prepared by reaction of 1-substituted 5-amino-1H-imidazole-4-carboxamides of the formula IV

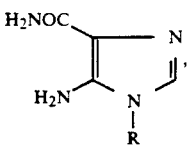

in which R has the same meaning as in formula I and in which hydroxyl groups, if any, in R may be acylated, with acylisothiocyanate and subsequent hydrolysis to remove the N-acyl group and any other acyl groups.

The compounds of formula IV can be prepared by alkylation of the known compound 5-amino-1H-imidazole-4-carboxamide in a known manner.

BEST MODE FOR CARRYING OUT THE INVENTION

The process according to the invention in variant a) is preferably carried out using a copper salt as the heavy metal salt. Hereby a high yield is obtained with a cheap reagent.

Moreover, the process in variant a) is advantageously carried out in the way that the aqueous alkaline medium is provided with an alkali metal hydroxide, preferably sodium or potassium hydroxide.

The process according to the invention in variant b) is preferably carried out using hydrogen peroxide as the peroxy compound.

PREPARATION OF STARTING MATERIALS

Preparation of
5-(N'-benzoylthiocarbamoyl)amino-1-methyl-1H-imidazole-4-carboxamide 5-Amino-1-methyl-1H-imidazole-4-carboxamide (6.5 g, 45 mM) and benzoylisothiocyanate (7.7 g, 47 mM) were refluxed in acetone (90 ml) for 4 hours under $N_2$. After cooling in an ice bath the formed product was filtered off, washed with acetone and dried. Hereby was isolated 13.0 g (95%) of the title compound as a white powder, mp 194°-196° C.

5-(N'-benzoylthiocarbamoyl)amino-1-ethyl-1H-imidazole-4-carboxamide was prepared in a similar manner from 5-amino-1-ethyl-1H-imidazole 4-carboxamide, mp. 178°-180° C.

5-(N'-benzoylthiocarbamoyl)amino-1-(1-propyl)-1-H-imidazole-4-carboxamide was prepared in a similar manner from 5-amino-1-(1-propyl)-1-H-imidazole-4-carboxamide, mp. 163°-164° C.

5-(N'-benzoylthiocarbamoyl)amino-1-benzyl-1H-imidazole-4-carboxamide was prepared in a similar manner from 5-amino-1-benzyl-1H-imidazole-4-carboxamide, mp. 181°-182.5° C.

1-[(2-Hydroxyethoxy)methyl]-5-(thiocarbamoyl)amino-1H-imidazole-4-carboxamide.

5-Amino-1-[[2-(acetyloxy)ethoxy]methyl]-1H-imidazole-4-carboxamide (44.0 g, 182 mM) and benzoylisothiocyanate (29.7 g, 182 mM) were refluxed in acetone (430 ml) for 1 hour. To the resulting solution were added methanol (430 ml) and potassium carbonate (14.9 g, 108 mM) dissolved in water (45 ml) whereafter the mixture was refluxed for 4 hours. After cooling to room temperature acetic acid was added to a pH-value of 8. The formed product was filtered off at 0° C., washed and dried. Hereby 39.2 g (83%) of the title compound was isolated as a white powder, mp. 181°-182° C. (dec.). A sample crystallized from water had mp. 182°-183° C. (dec.). $^{13}$C-NMR(DMSO-d$_6$) δppm: 183.9; 163.7; 134.9; 129.3; 127.9; 74.0; 70.4; 59.7.

Calculated for $C_8H_{13}N_5O_3S$: C 37.06%, H 5.05%, N 27.01%, S 12.37%
found: C 36.92%, H 5.07%, N 27.30%, S 12.28%.

1-[1,3-Dihydroxy-(2-propyloxy)methyl]-5-(thiocarbamoyl)amino-1-H-imidazole-4-carboxamide was prepared in a similar manner from 5-amino-[1,3-dihydroxy-(2-propyloxy)methyl]-1H-imidazole-4-carboxamide, mp. 185° C. (dec.). $^{13}$C-NMR(DMSO-d$_6$) δppm: 183.8; 163.9; 134.8; 129.2; 127.9; 80.2; 73.5; 60.7.

Calculated for $C_9H_{15}N_5O_4S$: C 37.36%, H 5.23%, N 24.21%, S 11.08%
found: C 37.34%, H 5.16%, N 23.81%, S 10.76%.

1-[(2-Hydroxyethoxy)methyl]-5-(thiocarbamoyl)amino-1H-imidazole-4-carboxamide.

Benzoylchloride (5.9 g, 42 mM) was, under $N_2$, added dropwise to a solution of ammoniumthiocyanate (3.2 g, 42 mM) in acetone (80 ml) at 25° C. in the course of 5 minutes. After reflux for 15 minutes it was cooled to 20° C., and the formed ammonium chloride was filtered off and washed with acetone (20 ml).

To the filtrate was added 5-amino-1-[[2-(acetyloxy)ethoxy]methyl]-1H-imidazole-4-carboxamide (9.7 g, 40 mM). The mixture was refluxed under $N_2$ for 90 minutes. Then methanol (80 ml) and potassium carbonate (5.8 g, 42 mM) dissolved in water (12 ml) were added and the mixture was refluxed for 8 hours under $N_2$. Water (70 ml) was added to the hydrolysis mixture, and it was treated with activated coal at 25° C. The solution was then evaporated to about 70 ml, and the pH-value adjusted to 7.0 with acetic acid. After cooling to 5° C. the resulting product was filtered off, washed with water and dried. Hereby was isolated 8.0 g (77%) of the title compound as a white powder, mp. 178°-180° C. (dec.). HPLC indicated >96% purity.

1-[(2-Hydroxyethoxy)methyl]-5-(thiocarbamoyl)amino-1H-imidazole-4-carboxamide.

Acetyl chloride (1.6 g, 21 mM) was, under $N_2$, added dropwise to a solution of ammonium thiocyanate (1.6 g, 21 mM) in acetone (30 ml) at 25° C. in the course of 5 minutes. After reflux for 15 minutes it was cooled to 20° C., and the formed ammonium chloride was filtered off and washed with acetone (10 ml).

To the filtrate was added 5amino-1-[[2-(acetyloxy)ethoxy]methyl]-1H-imidazole-4-carboxamide (4.8 g, 20 mM). The mixture was refluxed under $N_2$ for 20 hours. Then methanol (40 ml) and potassium carbonate (5.8 g, 42 mM) dissolved in water (12 ml) were added and the mixture was refluxed for 7 hours under $N_2$. Water (50 ml) was added to the hydrolysis mixture, and it was treated with activated coal at 25° C. The solution was then evaporated to about 30 ml and the pH-value adjusted to 7.0 with acetic acid. After cooling to 5° C. the formed product was filtered off, washed with water and dried. Hereby was isolated 3.2 g (62%) of the title compound as a white powder, mp. 175°-177° C. (dec.). HPLC indicated >94% purity.

1-Methyl-5-(thiocarbamoyl)amino-1H-imidazole-4-carboxamide.

5-(N'-benzoylthiocarbamoyl)amino-1-methyl-1H-imidazole-4-carboxamide (12.1 g, 40 mM) was added to a mixture of acetone and methanol (1:1) (200 ml). Potassium carbonate 2.8 g, 20 mM) dissolved in water (12 ml) was added. The reaction mixture was refluxed under $N_2$ for 6 hours whereafter acetic acid (2.9 g, 48 mM)

was added. After stirring in an ice bath the product was filtered off, washed and dried. Hereby was isolated 7.7 g (96%) of the title compound as a white powder, mp. 270°–274° C. (dec.) (the conversion begins at about 220° C.).

A sample crystallized from water melts at 280°–283° C. (dec.) (the conversion begins at about 220° C.). $^{13}$C-NMR(DMSO-d$_6$) δppm: 184.0; 163.9; 134.8; 130.2; 127.3; 30.9.

Calculated for $C_6H_9N_5OS$: C 36.17%, H 4.55%, N 35.16% found: C 36.06%, H 4.53%, N 35.05%

1-Ethyl-5-(thiocarbamoyl)amino-1H-imidazol-4-carboxamide was prepared in a similar manner from 5-(N'-benzoylthiocarbamoyl)amino-1-ethyl-1H-imidazole-4-carboxamide, mp. 265°–268° C. (dec.) $^{13}$C-NMR(DMSO-d$_6$) δppm: 183.8; 163.9; 133.8; 129.1; 127.8; 39.0; 15.2.

Calculated for $C_7H_{11}N_5OS$: C 39.42%, H 5.20%, N 32.84% found: C 39.37%, H 5.19%, N 32.71%

1-(1-propyl)-5-(thiocarbamoyl)amino-1H-imidazole-4-carboxamide was prepared in a similar manner from (5-(N'-benzoylthiocarbamoyl)amino-1-(1-propyl-1H-imidazole-4-carboxamide, mp. 197°–198° C. (dec.). $^{13}$C-NMR(DMSO-d$_6$) δppm: 183.8; 163.9; 134.4; 129.2; 127.7; 45.7; 22.7; 10.8.

Calculated for $C_8H_{13}N_5OS$: C 42.27%, H 5.77%, N 30.81% found: C 42.16%, H 5.84%, N 30.86%

1-Benzyl-5-(thiocarbamoyl)amino-1H-imidazole-4-carboxamide was prepared in a similar manner from 5-(N'-benzoythiocarbamoyl)amino-1-benzyl-1-H-imidazole-4-carboxamide, mp. 264°–266° C. (dec.) (the conversion begins at about 205° C. $^{13}$C-NMR(DMSO-d$_6$) δppm: 183.8; 163.9; 136.5; 134.5; 129.6; 128.6; 127.7; 127.4; 47.6.

Calculated for $C_{12}H_{13}N_5OS$: C 52.34%, H 4.76%, N 25.44% found: C 52.31%, H 4.73%, N 25.52%

The following examples illustrate the process according to the invention. Examples 1–7 illustrate process variant a), and examples 8–12 illustrate process variant b).

EXAMPLE 1

9-Methylguanine

1-Methyl-5-(thiocarbamoyl)amino-1H-imidazole-4-carboxamide (3.98 g, 20 mM) was dissolved in 1N sodium hydroxide (160 ml). Copper acetate, H$_2$O (4.6 g, 23 mM) was added and the reaction mixture as then refluxed for 1 hour. After cooling to 50° C. the formed copper sulphide was filtered off. The filtrate was acidified with acetic acid to pH 5.0. The resulting product was filtered off at 25° C. washed with water and dried. Hereby was isolated 3.16 g (96%) of the title compound as a white powder, mp. >300° C. $^{13}$C-NMR(1N NaOD) δppm: 170.7; 163.6; 154.0; 141.4; 120.0; 32.2.

Calculated for $C_6H_7N_5O$: C 43.63%, H 4.27%, N 42.41% found: C 43.05%, H 4.20%, N 41.95%

EXAMPLE 2

9-Ethylguanine

9-Ethylguanine was prepared in a similar manner from 1-ethyl-5-(thiocarbamoyl)amino-1H-imidazole-4-carboxamide, mp. >300° C.

Calculated for $C_7H_9N_5O$, $1/4H_2O$: C 45.77%, H 5.21%, N 38.13% found: C 45.52%, H 5.00%, N 38.04%

EXAMPLE 3

9-(1-Propyl)guanine 9-(1-Propyl)guanine was prepared in a similar manner from 1-(1-propyl)-5-(thiocarbamoy)amino-1H-imidazole-4-carboxamide, mp. >300° C. $^{13}$C-NMR(DMSO-d$_6$) δppm: 156.8; 153.3; 151.0; 137.4; 116.5; 44.2; 22.7; 10.8.

Calculated for $C_8H_{11}N_5O$: C 49.73%, H 5.74%, N 36.25% found: C 49.50%, H 5.76%, N 36.30%

EXAMPLE 4

9-Benzylguanine

9-Benzylguanine was prepared in a similar manner from 1-benzyl-5-(thiocarbamoyl)amino-1H-imidazole-4-carboxamide, mp. 305°–308° C. $^{13}$C-NMR(DMSO-d$_6$) δppm: 157.0; 153.8; 151.2; 137.6; 137.3; 128.7; 127.6; 127.2; 116.6; 45.9.

Calculated for $C_{12}H_{11}N_5O$: C 59.74%, H 4.59%, N 29.03% found C 59.50%, H 4.51%, N 28.91%

EXAMPLE 5a

9-[(2-Hydroxyethoxy)methyl]]guanine (Acyclovir)

1-[2-Hydroxyethoxy)methyl]-5-(thiocarbamoyl)amino-1H-imidazole-4-carboxamide (10.0 g, 38.6 mM) was added to a suspension of copper sulphate (7.0 g, 44 mM) in 6N sodium hydroxide (80 ml) and was stirred at room temperature for 4 hours. HPLC indicated 100% yield. After filtration 50% aqueous acetic acid (80 ml) was added to the filtrate. After a brief period of reflux the material was cooled to 5° C. The product was filtered off and crystallized from water, treatment being made with activated coal. Hereby was isolated 7.8 g (85%) 9-[(2-hydroxyethoxy)methyl] guanine, ¾ H$_2$O (Acyclovir) as a white powder. HPLC indicated >99% purity, mp. about 250° C. (dec.) $^{13}$C-NMR(DMSO-d$_6$) δppm: 156.8; 153.8; 151.4; 137.8; 116.5; 72.1; 70.4 and 59.9.

Calculated for $C_8H_{11}N_5O_3$, ¾ H$_2$O: C 40.25%, H 5.28%, N 29.34% found: C 40.39%, H 5.22%, N 29.37%.

EXAMPLE 5b

9-[(2-Hydroxyethoxy)methyl]guanine (Acyclovir).

1-[(2-Hydroxyethoxy)methyl]-5-(thiocarbomoyl)amino-1H-imidazole-4-carboxamide (1.30 g, 5.0 mM) was added to a suspension of copper acetate, H$_2$O (1.15 g, 5.75 mM) in 1N sodium hydroxide (60 ml) and refluxed for 30 minutes. HPLC indicated 100% yield. After filtration acetic acid (5 ml) was added to the filtrate, and then heating with activated coal was performed. The coal was filtered off, whereafter the material was cooled to 5° C. The precipitated product was filtered off, washed with water and dried. Hereby was isolated 0.92 g (77%) of 9-[(2-hydroxyethoxy)methyl]-quanine, ¾ H$_2$O as a white powder. HPLC indicated >99% purity.

The use of other heavy metal salts and varying amounts of sodium hydroxide in the process of example 5 is illustrated by the following table.

Preparation of Acyclovir

1-[(2-Hydroxyethoxy)methyl]5-(thiocarbamoyl)amino-1H-imidazole-4-carboxamide 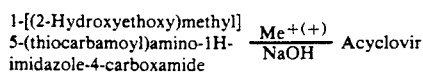 Acyclovir

| Metal ion moles | Conc. NaOH N | Moles NaOH/ moles start. comp. | re- action temp. °C. | reaction time hours | yield acc. to HPLC % | iso- lated yield % |
| --- | --- | --- | --- | --- | --- | --- |
| Cu++(1.15) | 0.1 | 4 | 100 | 2 | 42 | — |
| Cu++(1.15) | 0.1 | 12 | 100 | 1 | 88 | — |
| Cu++(1.15) | 1.0 | 6 | 25 | 45 | 94 | — |
| Cu++(1.15) | 1.0 | 6 | 100 | 1 | 97 | — |
| Cu++(1.15) | 1.0 | 12 | 100 | 0.5 | 100 | 77 |
| Cu++(1.15) | 3.0 | 12 | 0 | 45 | 95 | — |
| Cu++(1.15) | 6.0 | 12 | 25 | 4 | 100 | 85 |
| Cu++(1.15) | 6.0 | 12 | 25 | 2 | 100 | 84 |
| Hg++(1.15) | 3.0 | 12 | 100 | 0.5 | 87 | — |
| Ag+(2.30) | 3.0 | 12 | 100 | 2 | 100 | — |
| Pb++(1.15) | 3.0 | 12 | 100 | 2 | 26 | — |

EXAMPLE 6

9-[1,3-Dihydroxy-(2-propyloxy)methyl]quanine

1-[1,3-Dihydroxy-(2-propyloxy)methyl]-5-(thiocarbamoyl)amino-1H-imidazole-4-carboxamide (0.58 g, 2.0 mM) was added to a suspension of copper sulphate (0.32 g, 2.3 mM) in 3N sodium hydroxide (8 ml) and refluxed for 1 hour. HPLC indicated 100% yield. After filtration 33% aqueous acetic acid (6 ml) was added to the filtrate, and it was refluxed again while being treated with activated coal. The coal was filtered off and the solution was cooled to 5° C. Filtration, washing with water and drying resulted in 0.33 g (62%) of 9-[1,3-dihydroxy-(2-propyloxy)methyl]quanine, 3/4 $H_2O$ as a white powder, mp. about 245° C. (dec.). $^{13}$C-NMR(DMSO-$d_6$) δppm: 157.0; 153.9; 151.3; 137.6; 116.3; 79.9; 71.4; 60.8.

Calculated for $C_9H_{13}H_5O_4$, ¾ $H_2O$: C 40.22%, H 5.43%, N 26.06% found: C 40.25%, H 5.31%, N 25.58%.

EXAMPLE 7

9-β-D-Ribofuranosyl guanine (guanosine)

5-Amino-1-(β-D-ribofuranosyl)-1H-imidazole-4-carboxamide (5.0 g, 19.4 mM) and benzoylisothiocyanate (3.3 g, 20 mM) was stirred at room temperature in DMF (40 ml) for 1 hour. The solvent was stripped off in water-jet vacuo. The residue was dissolved in methanol (160 ml) and potassium carbonate (1.6 g, 11.6 mM) in water (8 ml) was added whereafter the mixture was refluxed at 2 hours. After cooling to room temperature acetic acid was added to pH 6. The reaction mixture was evaporated in water-jet vacuo, and the residue was crystallized from ethanol. Hereby was isolated 5.0 g of crude 1-(β-D-ribofuranosyl)-5-(thiocarbamoyl)amino-1H-imidazole-4-carboxamide. HPLC indicated a purity of about 65% (the remaining 35% was essentially potassium acetate).

The crude product of 1-(β-D-ribofuranosyl)-5-(thiocarbamoyl)amino-1H-imidazole-4-carboxamide (5.0 g) was added to a suspension of copper sulphate (2.9 g, 18 mM) in 3N sodium hydroxide (60 ml) and refluxed for 1 hour. After filtration 33% aqueous acetic acid (30 ml) was added to the filtrate and it was refluxed again while being treated with activated coal. The coal was filtered off, and the solution was cooled to room temperature overnight. Filtration, washing with water and drying gave 2.0 g (65%) of 9-β-D-ribofuranosyl guanine, $H_2O$ (guanosine, $H_2O$) as a white powder, mp. 250° C. (dec.). The product had the same physical data as an authentic sample of guanosine, $H_2O$.

EXAMPLE 8

9-(1-Propyl)guanine 1-(1-Propyl)-5-thiocarbamoyl)amino-1H-imidazole-4-carboxamide (1.14 g, 5.0 mM) and sodium tungstate (0.2 g) were dissolved in 1N sodium hydroxide (50 ml) at 0° C. 35% hydrogen peroxide (1.8 ml, 20 mM) in water (5 ml) was added dropwise at 0°-10° C. in the course of 30 minutes. After stirring in an ice bath for 1 hour pH was adjusted to 5 with acetic acid. The formed product was filtered off, washed with water and dried. Hereby was isolated 0.41 g (42%) of the title compound as a white powder. HPLC indicated >98% purity. The product had the same physical data as the product of example 3.

EXAMPLE 9

9-Benzylguanine

1-Benzyl-5-(thiocarbamoyl)amino-1H-imidazole-4-carboxamide (2.75 g, 10.0 mM) and sodium tungstate (0.1 g) were suspended in 6N sodium hydroxide (20 ml) at 5° C. 35% hydrogen peroxide (4.0 ml, 44 mM) was added dropwise at 5°-15° C. over 30 minutes. Water (60 ml) was added to the resulting reaction mixture. After stirring for 1 hour in an ice bath pH was adjusted to 5 with hydrochloric acid. The formed product was filtered off, washed with water and dried. Hereby was isolated 1.30 g (54%) of the title compound as a white powder. HPLC indicated about 98% purity. The product had the same physical data as the product of example 4.

EXAMPLE 10

9-Methylguanine

9-Methylguanine was prepared in a similar manner from 1-methyl-5-(thiocarbamoyl)amino-1H-imidazole-4-carboxamide. The product had the same physical data as the product of example 1.

EXAMPLE 11

9-Ethylguanine

9-Ethylguanine was prepared in a similar manner from 1-ethyl-5-(thiocarbamoyl)amino-1-imidazole-4-carboxamide. The product had the same physical data as the product of example 2.

EXAMPLE 12

9-[(2-Hydroxyethoxy)methyl]guanine (Acyclovir)

1-[(2-Hydroxyethoxy)methyl]-5-(thiocarbamoyl)amino-1H-imidazole-4-carboxamide (2.59 g, 10.0 mM) and sodium tungstate (0.05 g) were dissolved in 6N sodium hydroxide (20 ml) at 5° C. 35% hydrogen peroxide (4.0 ml, 44 mM) was added dropwise at 5°-15° C. in the course of 15 minutes. After stirring for 15 minutes at 0°-5° C. HPLC indicated 59% yield of the title compound. The pH-value of the reaction mixture was adjusted to 5.5 with 25% aqueous acetic acid. The resulting product was filtered off, washed with water and dried which gave 1.13 g (50%) of the title compound as a white powder. HPLC indicated a purity of about 97%. The product had the same physical data as the product of example 5.

I claim:

1. A process for the preparation of 9-substituted guanine derivatives of formula I

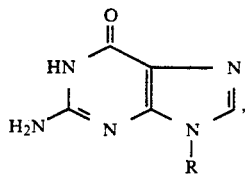

in which R is $C_1$–$C_4$-alkyl, optionally substituted with one or more hydroxy groups, or R is

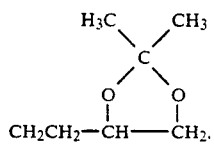

benzyl, ribosyl, 2'-deoxyribosyl or $(CH_2)_n$-$OR^1$ where n is 1 or 2, and $R^1$ is $CH_2CH_2OH$ or

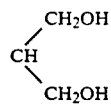

and pharmaceutically acceptable salts thereof, comprising the steps of cyclizing a 1-substituted 5-(thiocarbamoyl)amino-1H-imidazole-4-carboxamide of formula III

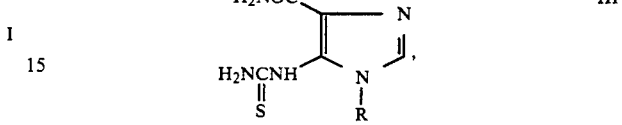

where R has the same meaning as in formula I
 a) by treatment with a heavy metal salt selected from the group consisting of Cu-, Ag-, Pb- and Hg-salts in an aqueous alkaline medium containing at least four equivalents of $OH^-$ ions at a temperature from about 0° C. to the reflux temperature, or
 b) by treatment with a peroxy compound in an aqueous alkaline medium at a temperature of about 0°–30° C., whereafter I is isolated by treatment with acid, and, if desired, is converted into a pharmaceutically acceptable salt.

2. A process as claimed in claim 1 a) wherein the heavy metal salt is a copper salt.

3. A process as claimed in claim 1, wherein compounds of formula (I) are cyclized by treatment with a peroxy compound in an aqueous alkaline medium at a temperature of about 0°–30° C., wherein the peroxy compound is hydrogen peroxide, and the cyclization is carried out in the presence of tungstate ions as catalyst.

* * * * *